United States Patent [19]

Bublitz

[11] B  3,985,894
[45]  Oct. 12, 1976

[54] METHOD OF CONTROLLING RICE BLAST WITH N-(ALKYLTHIOPHENYL)MALEIMIDES
[75] Inventor: Donald E. Bublitz, Concord, Calif.
[73] Assignee: The Dow Chemical Company, Midland, Mich.
[22] Filed: Aug. 9, 1974
[21] Appl. No.: 496,431
[44] Published under the second Trial Voluntary Protest Program on January 13, 1976 as document No. B 496,431.

Related U.S. Application Data
[62] Division of Ser. No. 307,608, Nov. 17, 1972, Pat. No. 3,853,912.

[52] U.S. Cl. .............................................. 424/274
[51] Int. Cl.$^2$........................................... A01N 9/22
[58] Field of Search ................................... 424/274

[56]  References Cited
UNITED STATES PATENTS

| 2,205,558 | 6/1940 | Flett ............................. 424/274 X |
| 3,129,225 | 4/1964 | Shapiro et al. .................. 424/274 X |

Primary Examiner—Stanley J. Friedman
Assistant Examiner—Daren M. Stephens
Attorney, Agent, or Firm—Edward E. Schilling

[57]  ABSTRACT

Disclosed are N-(alkylthiophenyl)maleimide compounds useful for controlling rice blast on rice plants.

11 Claims, No Drawings

METHOD OF CONTROLLING RICE BLAST WITH N-(ALKYLTHIOPHENYL)MALEIMIDES

CROSS REFERENCE TO RELATED APPLICATION

This is a division of application Ser. No. 307,608 filed Nov. 17, 1972, now U.S. Pat. No. 3,853,912.

BACKGROUND OF THE INVENTION

1. Field of the Invention

This invention relates to novel N-(alkylthiophenyl)-maleimide compounds and to compositions and methods employing such compounds in the control of rice blast.

2. Description of the Prior Art

The present invention is useful in the control and prevention of agricultural plant diseases, particularly in the control of rice blast (*Piricularia oryzae*) which is the most hazardous pest in rice plant. In order to prevent the rice blast, organomercury compounds such as phenyl mercuric acetate and phenyl mercuric iodide have been previously employed.

However, organomercury compounds and organometallic compounds in general are residual and accumulate in the soil of treated fields and in rice hulls and thus pose environmental as well as public health problems.

Other non-metallic organo compounds known in the art also suffer disadvantages which proscribe their use as agricultural fungicides. The most serious drawback suffered with compounds possessing fungicidal activity is their phytotoxicity to the host rice plant at desired dosage rates employed. N-(2'-methoxyphenyl)maleimide (the synthesis of which is described in Chem. Abstracts 52:9025a; see also U.S. Pat. No. 2,205,588) is an example of such a compound which, while found to be active against rice blast by the applicant, cannot be safely employed due to its high phytotoxicity to the host rice plant.

SUMMARY OF THE INVENTION

It has now been found in accordance with the present invention that particular novel substituted maleimide compounds having the formula:

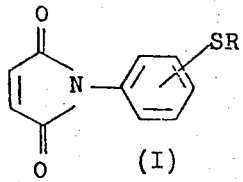

wherein SR is in the ortho- or meta- position; and R is an alkyl group of from 1 to 6 carbon atoms, both inclusive, and compositions containing such compounds are particularly effective in controlling rice blast without injury to the host rice plant. The present invention also provides a method for combatting rice blast which comprises contacting said plants to be protected with a rice blast controlling amount of at least one compound of the following formula:

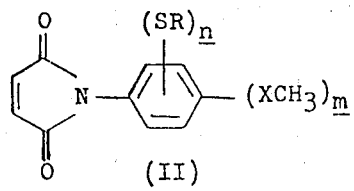

wherein
—$(SR)_n$ is in the ortho or meta position;
$n$ is 0 or 1;
$m$ is 0 or 1, with the proviso that the sum of $n + m$ is always 1;
R is an alkyl group of from 1 to 6 carbon atoms;
and X is oxygen or sulfur.

It is very surprising that the maleimide compounds usable according to the present invention can be safely employed without injury to the host plant at dosage rates at which known prior art compounds are phytotoxic to the host plant. The active compounds according to the present invention thus constitute a valuable addition to the art.

DESCRIPTION OF THE PREFERRED EMBODIMENTS

The term "alkyl" as used herein means both straight and branched chain radicals containing from 1 to 6 carbon atoms, as illustrated by, but not limited to, methyl, ethyl, propyl, isopropyl, butyl, isobutyl, amyl, isoamyl, hexyl or the like. Preferred species of the present invention include those maleimide compounds of Formula I wherein R is alkyl of 1 to 3 carbon atoms. Further preferred are the maleimide compounds wherein R is methyl. Especially preferred are the maleimide compounds wherein SR is in the ortho position.

The instant maleimide compounds of the present invention are obtained by the process which comprises reacting maleic anhydride with an alkylmercaptoaniline compound in the presence of an inert carrier such as, for example, ethyl ether, methylene chloride or the like, to produce a corresponding alkylmercaptomaleanilic acid intermediate. The intermediate thus obtained is subsequently dehydrated by conventional procedures to produce the desired N-(alkylthiophenyl)maleimide. The reaction directed to the preparation of the alkylmercaptomaleanilic acid intermediate takes place readily at a temperature of from about 20°C. to the reflux temperature of the reaction mixture, preferably at temperatures of from about 20° to about 50°C.

The proportions of the maleic anhydride and alkylmercaptoaniline to be employed are not critical, some of the desired intermediate being formed upon contacting these reactants in any proportions. However, the reaction consumes the maleic anhydride and alkylmercaptoaniline starting materials in equimolar proportions and the use of the starting materials in about such proportions is preferred.

In carrying out the production of the desired product, the maleic anhydride and alkylmercaptoaniline are contacted together in any order or fashion. In a convenient procedure, the alkylmercaptoaniline reactant is slowly added portionwise to a solution of maleic anhydride and carrier medium. The temperature of the reaction mixture is then maintained within the reaction temperature range for a short period of time. During the reaction period the alkylmercaptomaleanilic acid intermediate begins to precipitate in the reaction mixture. Following the reaction period the reaction mixture can be cooled to insure that most of the intermediate is precipitated.

The dehydration of the alkylmercaptomaleanilic acid is accomplished by contacting the aforesaid intermediate with acetic anhydride and sodium acetate in the presence of an inert carrier, such as hereinbefore mentioned. The resulting reaction mixture is heated at a temperature from 60°–120°C. with the production of the desired product. The desired N-(alkylthiophenyl)-maleimide product is isolated by such conventional procedures as diluting the dehydration mixture with water in order to precipitate the desired product, the latter thereafter being collected by filtration or decantation. In another representative procedure, the reaction mixture can be distilled to remove the low boiling constituents and obtain the N-(alkylthiophenyl)maleimide product as a residue. This product can be further purified by such procedures as washing with water or recrystallization from an organic solvent.

In carrying out the preparation of the compound of the present invention, it has been found to be unnecessary to isolate the alkylmercaptomaleanilic acid intermediate. This intermediate can be dehydrated in the reaction mixture in which it was originally formed by the addition of acetic anhydride and sodium acetate to the reaction mixture following the production of the desired intermediate and heating the reaction mixture to a temperature of from 60° to 120°C. The desired N-(alkylthiophenyl)maleimide product is then separated from the reaction mixture as previously described.

The invention will be further explained in detail with reference to the following examples.

EXAMPLE 1

A mixture of 2-methylmercaptoaniline (11.7 grams) in 30 milliliters (ml.) of ethyl ether was added dropwise with stirring to a solution of maleic anhydride (8.26 grams) in 90 ml. of ethyl ether. During the contacting of the reactants and for a period of about one hour thereafter, the reaction mixture was heated at the boiling temperature and under reflux. Following the heating period, the reaction mixture was cooled. During the reaction the 2-methylthiomaleanilic acid product precipitated in the reaction mixture as a crystalline solid. This solid was removed from the reaction mixture by filtration and dried (melting point 121°C.).

The 2-methylthiomaleanilic acid (8.6 grams) obtained by filtration was suspended in a mixture of 2.0 grams of sodium acetate and 25 ml. of acetic anhydride. The resulting mixture was heated at about 90°C. for a period of one-half hour on a steam bath. Following the heating period, the reaction mixture was cooled and thereafter diluted with water. During the dilution, the desired N-(2'-methylthiophenyl)maleimide product precipitated from the diluted reaction mixture and was removed therefrom by filtration. The product was thereafter dried and found to melt at a temperature of 84°–88°C.

Analysis calculated for $C_{11}H_9NO_2S$: C, 60.2; H, 4.1; N, 6.4. Found: C, 60.7; H, 4.6; N, 6.8.

In accordance with the procedures and reactants employed in Example 1 above, the replacement of 2-methylmercaptoaniline with:
 3-methylthioaniline;
 4-methylthioaniline;
 2-isopropylthioaniline;
 2-n-pentylthioaniline;
 3-ethylthioaniline;
 3-n-butylthioaniline; and
 3-n-hexylthioaniline,
yields the following compounds of the present invention:
 N-(3'-methylthiophenyl)maleimide (melting at 54°C.);
 N-(4'-methylthiophenyl)maleimide (melting at 104°C.);
 N-(2'-isopropylthiophenyl)maleimide (molecular weight 247.2);
 N-(2'-n-pentylthiophenyl)maleimide (molecular weight 275.2);
 N-(3'-ethylthiophenyl)maleimide (molecular weight 233.2);
 N-(3'-n-butylthiophenyl)maleimide (molecular weight 261.2); and
 N-(3'-n-hexylthiophenyl)maleimide (molecular weight 289.2).

The foregoing compounds are suitable for use in the control of rice blast in the form obtained from the reaction mixture; however, the compounds may be further purified by recrystallization or other conventional techniques to obtain the highly purified compound if desired.

The reactants employed herein are known materials which are either readily available or which can be prepared according to known or analogous procedures set forth in the art. The maleimide compound of Formula II wherein m is 1 and X is oxygen is known in the art; see Chem. Abstracts 50:3420e, wherein the synthesis of such compound is described. The compound is also generically taught in U.S. Pat. No. 2,205,588. However, there are no literature references to the use of N-(4'-methoxyphenyl)maleimide as a rice blast control agent.

The maleimide compounds of Formulas (I) and (II) are useful as fungicidal agents in the control of rice blast. For such uses, the unmodified compound can be utilized. However, the present invention also embraces the use of such compounds with inert solid or liquid agriculturally acceptable carriers. Thus, for example, a compound can be dispersed on a finely divided solid and employed therein as a dust. Also, the compounds, or a solid composition comprising the compound, can be dispersed in water, typically with the aid of a wetting agent, and the resulting aqueous suspension employed as a spray, drench or wash. In other procedures, the compound can be employed as a constituent of organic liquid compositions, oil-in-water and water-in-oil emulsions, or water dispersions, with or without the addition of wetting, dispersing, or emulsifying agents.

It is to be understood, however, that all of the compounds claimed and compositions containing them may not be equally effective at similar concentrations. The exact concentration of the toxic compound to be employed in the treating compositions is not critical and may vary considerably provided rice plants are contacted with a rice blast controlling amount of the maleimide compound or compounds employed. The concentration of the toxicants in liquid compositions generally is from about 1.0 to about 50 percent by weight, although concentrations of up to about 95 weight percent are often employed. In dusts or dry formulations, the concentration of the toxicant can be from about 1.0 to about 10 weight percent; however, concentrations up to about 95 weight percent are often conveniently employed. In compositions to be employed as concentrates, the toxicant can be present in a concentration of from 5 to about 98 weight percent.

The compounds of this invention can also be employed in admixture with one another or applied admixed with other chemicals which are used in agronomic and horticultural management and are compatible with the compounds of this invention. Such chemicals can be, but are not restricted to, the classes of chemicals commonly known as plant nutrients, fertilizers, insecticides and other fungicides, which are not phytotoxic to the host rice plant.

Each of the compounds of the present invention, the utility of which is not specifically recited hereinafter, has the ability to inhibit or otherwise control rice blast when applied at dosage levels of from about 150 to about 600 or more parts per million by weight.

EXAMPLE 2

Separate aqueous compositions containing N-(2'-methylthiophenyl)maleimide and N-(3'-methylthiophenyl)maleimide, are prepared by mixing 4 parts by weight of the compound, 0.08 part by weight of sorbitan trioleate (Span 85), and 0.02 part of sorbitan monooleate polyoxyethylene derivative (Tween 80) are dispersed in 40 milliliters of acetone to produce a concentrate composition in the form of a water-dispersible liquid containing one of the test compounds as the sole active agent.

EXAMPLE 3

A portion of each of the concentrate compositions prepared in Example 2 is diluted with 20% isopropanol to provide liquid compositions containing from 150 to 600 parts per million by weight of active compound. Rice plant seedlings 10 to 15 days old (variety, Caloro) were sprayed with the prepared dispersions; after natural drying, the plants were inoculated with an inoculum of rice blast spores (Piricularia oryzae) in 10% isopropyanol. The inoculated plants were maintained under conditions conducive to germination of rice blast spore and growth for a period of 10 days. After the 10 day period, the plants were microscopically examined and the lowest amount of active ingredient showing 90% of prevention of spore germination determined. As a result of such operations, it was found that both of the N-(2'-methylthiophenyl)maleimide and N-(3'-methylthiophenyl)maleimide test compounds had an $LD_{90}$ of 150 parts per million. No phytotoxic effects on the host rice plants were observed at the 150 or 600 part per million concentrations employed.

In comparative operations, separate concentrate compositions containing each of the N-(2'-methoxyphenyl)maleimide and N-(3'-methylphenyl)maleimide art compounds were prepared as in Example 2 and diluted as above to prepare treating compositions containing from 150 to 600 parts per million by weight of the test compound. The prepared compositions were employed in similar rice blast spore treating operations as described above. The examination following the 10 day period indicated that, while the N-(2'-methoxyphenyl)maleimide compound had an $LD_{90}$ of 150 parts per million by weight and the N-(3'-methylphenyl)maleimide compound had an $LD_{90}$ of 600 parts per million, both compounds were phytotoxic to the host rice plants at the indicated dosage rates.

EXAMPLE 4

The procedures and operations of Examples two and three above were repeated using N-(4'-methoxyphenyl)maleimide and N-(4'-methylthiophenyl)maleimide as the active test compounds. As a result of such operations, it was found that each of the test compounds was effective in preventing 90% of rice blast spore germination at a concentration of 150 parts per million; no phytotoxic effects on the host rice plants were observed at such concentration.

EXAMPLE 5

Forty-five parts by weight of N-(2'-methylthiophenyl)maleimide is mixed and ground with 5 parts by weight of Triton-155 to prepare a water-dispersible concentrate composition containing 90 percent by weight of the maleimide compound.

In a further operation, 25 parts by weight of N-(3'-methylthiophenyl)maleimide and 10 parts by weight of Triton-155 and 65 parts by weight of xylene are mixed together to prepare an emulsifiable concentrate composition containing 25 percent by weight of the maleimide compound.

In a similar manner, 25 parts by weight of N-(2'-methylthiophenyl)maleimide and 71 parts of fuller's earth, 2 parts of alkyl aryl sulfonate (Nacconol NR) and 2 parts of a polymerized sodium salt of a substituted benzoid alkyl sulfonic acid (Daxad No. 27) are mechanically mixed and ground together to prepare a concentrate in the form of a wettable powder and containing 25 percent by weight of the maleimide compound.

A mixture of 20 parts by weight N-(3'-methylthiophenyl)maleimide, 0.1 part of Nacconol NR, 0.1 part Daxad No. 27, and 100 parts of water and ball-milled together to prepare a water-dispersible liquid concentrate composition containing 20 parts by weight of the maleimide compound.

The compositions thus prepared can be dispersed in water to prepare aqueous compositions which have very desirable wetting and penetrating properties and are adapted to distribute effective amounts of the desired maleimide compound for control of rice blast on rice plants.

All starting materials employed in the preparation of the maleimide compounds of the present invention are known and are either readily available or can be prepared according to known or analogous procedures set forth in the prior art.

While this invention has been described and exemplified in terms of its preferred embodiment, those skilled in the art will appreciate that modifications can be made without departing from the spirit and scope of the invention.

I claim:

1. A composition comprising an inert agricultural acceptable carrier and a rice-blast controlling amount of a compound of the formula:

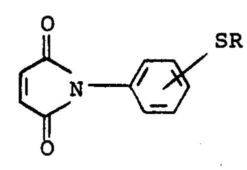

wherein SR is in the ortho- or meta- position and R is methyl.

2. The composition of claim 1 wherein the compound is N-(2'-methylthiophenyl)maleimide.

3. The composition of claim 1 wherein the compound is N-(3'-methylthiophenyl)maleimide.

4. A method for controlling rice blast on a rice plant comprising applying to the plant to be protected a rice blast controlling amount of a compound having the formula:

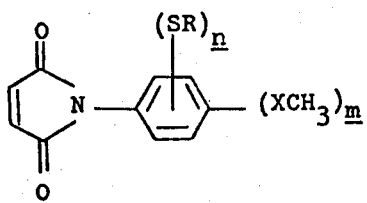

wherein $-(SR)_n$ is in the ortho or meta position; $n$ is 0 or 1; $m$ is 0 or 1, with the proviso that the sum of $n +$ $m$ is always 1; R is an alkyl group of from 1 to 6 carbon atoms; and X is oxygen or sulfur.

5. The method of claim 4 wherein $n$ is 1.
6. The method of claim 4 wherein $m$ is 1.
7. The method of claim 4 wherein $-(SR)_n$ is in the ortho position.
8. The method of claim 4 wherein the compound is N-(2'-methylthiophenyl)maleimide.
9. The method of claim 4 wherein the compound is N-(3'-methylthiophenyl)maleimide.
10. The method of claim 4 wherein the compound is N-(4'-methylthiophenyl)maleimide.
11. The method of claim 4 wherein the compound is N-(4'-methoxyphenyl)maleimide.

* * * * *